United States Patent
Madhavan (10) Patent No.: US 12,343,136 B2
(45) Date of Patent: Jul. 1, 2025

(54) PORTABLE SYSTEMS AND METHODS FOR ANKLE REHABILITATION

(71) Applicant: THE BOARD OF TRUSTEES OF THE UNIVERSITY OF ILLINOIS, Urbana, IL (US)

(72) Inventor: Sangeetha Madhavan, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 821 days.

(21) Appl. No.: 17/293,468

(22) PCT Filed: Nov. 13, 2019

(86) PCT No.: PCT/US2019/061264
§ 371 (c)(1),
(2) Date: May 12, 2021

(87) PCT Pub. No.: WO2020/102411
PCT Pub. Date: May 22, 2020

(65) Prior Publication Data
US 2022/0125341 A1  Apr. 28, 2022

Related U.S. Application Data

(60) Provisional application No. 62/760,798, filed on Nov. 13, 2018.

(51) Int. Cl.
*A61B 5/11*    (2006.01)
*A61B 5/00*    (2006.01)
(Continued)

(52) U.S. Cl.
CPC .......... *A61B 5/1124* (2013.01); *A61B 5/4528* (2013.01); *A61B 5/4595* (2013.01);
(Continued)

(58) Field of Classification Search
CPC ... A61B 5/1124; A61B 5/4528; A61B 5/5695; A61B 5/742; A61B 5/1121;
(Continued)

(56) References Cited

U.S. PATENT DOCUMENTS 5,989,157 A * 11/1999 Walton ............... A63B 71/0622
482/4
2002/0143277 A1 * 10/2002 Wood ..................... A61B 5/486
600/595

(Continued)

FOREIGN PATENT DOCUMENTS

WO    2017/216043    12/2017

OTHER PUBLICATIONS

Karime, Ali, et al. "Tele-Wobble: A telerehabilitation wobble board for lower extremity therapy." IEEE Transactions on Instrumentation and Measurement 61.7 (2012): 1816-1824. (Year: 2012).*

(Continued)

*Primary Examiner* — Jennifer Robertson
*Assistant Examiner* — Nidhi N Patel
(74) *Attorney, Agent, or Firm* — McDonnell Boehnen Hulbert & Berghoff LLP (57) ABSTRACT

The present disclosure provides methods and systems for improved rehabilitation of ankle motion by visually-driven priming of motor movement. The methods and systems include a sensor configured to measure ankle angle. The generated signal may be used to determine a maximal range of angles the user is capable of generating in order to calibrate the system. Subsequently, the signal from the sensor may be used to display the user location relative to an indication used to prime the motor movement. User performance may be tracked and performance-based awards given to increase rehabilitative outcome. The method and systems (Continued)

may encourage increased patient compliance by providing a comfortable, effective mode of ankle rehabilitation.

20 Claims, 9 Drawing Sheets

(51) Int. Cl.
    *G09B 19/00*     (2006.01)
    *G16H 20/30*     (2018.01)
    *G16H 40/60*     (2018.01)
(52) U.S. Cl.
    CPC .......... *A61B 5/742* (2013.01); *A61B 2505/09* (2013.01); *G09B 19/0038* (2013.01); *G16H 20/30* (2018.01); *G16H 40/60* (2018.01)
(58) Field of Classification Search
    CPC ............ A61B 2505/09; G09B 19/0038; G16H 20/30; G16H 40/60
    See application file for complete search history.

(56) References Cited

U.S. PATENT DOCUMENTS

| | | |
|---|---|---|
| 2010/0280418 A1 | 11/2010 | Klose |
| 2012/0130280 A1* | 5/2012 | Lee ..................... A61B 5/1121 |
| | | 600/587 |
| 2017/0136296 A1 | 5/2017 | Barrera et al. |
| 2018/0121728 A1 | 5/2018 | Wells et al. |
| 2018/0256939 A1 | 9/2018 | Malcolm |

OTHER PUBLICATIONS

Gian, Kah Shin Michelle, et al. "A Game-Based Approach for Hemiplegia Lower Limb Rehabilitation." 2018 2nd International Conference on BioSignal Analysis, Processing and Systems (ICBAPS). IEEE, 2018. (Year: 2018).*

The International Search Report (ISR) with Written Opinion for PCT/US2019/061264 dated Feb. 25, 2020, pp. 1-19.

* cited by examiner

PORTABLE SYSTEMS AND METHODS FOR ANKLE REHABILITATION

CROSS-REFERENCE TO RELATED APPLICATION

This application is a U.S. national phase of International Application No. PCT/US2019/061264, filed on Nov. 13, 2019, which claims priority to U.S. Provisional Application No. 62/760,798, filed Nov. 13, 2018, both of which are incorporated by reference herein in their entirety.

BACKGROUND

The future of neurorehabilitation lies in addressing the many difficulties associated with improving mobility and mental processing for post-stroke patients. Of particular interest is the restoration of the ability to smoothly coordinate movement of the lower extremities, especially the ankle. Ankle function is often impaired following a brain injury, such as a stroke, which can lead to difficulty in moving, loss of balance, and an increased risk of falling. Rehabilitation exercises are critical to regaining functional use of the ankle joint. Of particular relevance to rehabilitation is the practice of movement priming, where a patient is exposed to a stimulus indicating how to move the affected joint and must motor plan how to respond. Priming can be categorized as a restorative intervention that reduces impairment by targeting underlying neural mechanisms in neurological disorders. Movement priming has been shown to facilitate motor learning and cause changes in neuroplasticity, aiding rehabilitation.

A key obstacle to effective rehabilitation, including that via movement priming, is patient compliance. Rehabilitation exercises often include long periods of repetitive exercises and utilize specialized machinery that often cannot be brought to a residential setting. Such factors lead to low compliance and poor rehabilitation outcomes. Therefore, there exists a need to provide engaging, motivating rehabilitation exercises to increase patient participation. Additionally, there exists a need for inexpensive, portable rehabilitation devices that can be safely and effectively used inside or outside of a clinical setting.

SUMMARY

An aspect of the present disclosure relates to a method for improved rehabilitation of ankle motion by visually-driven priming of motor movement, the method comprising (i) operating a sensor to generate a first signal representative of ankle angle over a first period of time; (ii) determining, based on the first signal, a range of angles detected over the first period of time; (iii) operating a display to provide an indication to prime a repetitive motor movement, wherein the indication represents at least a portion of the repetitive motor movement; (iv) operating the sensor to generate a second signal representative of ankle angle over a second period of time; (v) during the second period of time, mapping the second signal to a user location relative to the repetitive motor movement; (vi) during the second period of time, operating the display to update the indication that represents the repetitive motor movement, wherein operating the display to update the indication that represents the repetitive motor movement includes updating a location, relative to the representation of the repetitive motor movement, of a cursor according to the user location.

Another aspect of the present disclosure relates to a non-transitory computer-readable medium, having stored thereon program instructions that, upon execution by the controller, cause the controller to perform the method as otherwise described herein.

Another aspect of the present disclosure relates to a system comprising (i) a sensor configured to measure an ankle angle; (ii) a display; (iii) a controller comprising at least one processor, wherein the controller is configured to perform operations including: (a) operating a sensor to generate a first signal representative of ankle angle over a first period of time; (b) determining, based on the first signal, a range of angles detected over the first period of time; (c) operating a display to provide an indication to prime a repetitive motor movement, wherein the indication represents at least a portion of the repetitive motor movement; (d) operating the sensor to generate a second signal representative of ankle angle over a second period of time; (e) during the second period of time, mapping the second signal to a user location relative to the repetitive motor movement; (f) during the second period of time, operating the display to update the indication that represents the repetitive motor movement, wherein operating the display to update the indication that represents the repetitive motor movement includes updating a location, relative to the representation of the repetitive motor movement, of a cursor according to the user location.

Another aspect of the present disclosure relates to a system comprising (i) a sensor configured to measure an ankle angle; (ii) a display; (iii) a controller comprising at least one processor; (iv) a non-transitory computer-readable medium, having stored thereon program instructions that, upon execution by the controller, cause the controller to perform the method as otherwise described herein.

These as well as other aspects, advantages, and alternatives will become apparent to those of ordinary skill in the art by reading the following detailed description with reference where appropriate to the accompanying drawings. Further, it should be understood that the description provided in this summary section and elsewhere in this document is intended to illustrate the claimed subject matter by way of example and not by way of limitation.

Other embodiments not shown herein are contemplated.

DETAILED DESCRIPTION

Examples of methods and systems are described herein. It should be understood that the words "exemplary," "example," and "illustrative," are used herein to mean "serving as an example, instance, or illustration." Any embodiment or feature described herein as "exemplary," "example," or "illustrative," is not necessarily to be construed as preferred or advantageous over other embodiments or features. Further, the exemplary embodiments described herein are not meant to be limiting. It will be readily understood that certain aspects of the disclosed systems and methods can be arranged and combined in a wide variety of different configurations.

I. Overview

Visually-driven priming of motor movement typically includes a stimulus to indicate to the patient a motor function that is about to be performed. In a rehabilitation scenario, this motor function typically centers around the function of a body part that has been impaired (e.g., by trauma to the body part itself, or by ischemic or other varieties of damage to a portion of the brain or nerves associated with the body part). Recent research suggests that visually-driven priming of motor movement leads to implicit motor learning and increases in neuroplasticity. Such effects can, in turn, lead to increased motor function. Several criteria must be addressed in order to successfully prime a motor movement. First, the action should be anticipated, that is, the patient should be shown the movement to be completed some length of time before the movement actually needs to occur. Second, the movement should be repetitive. Repetitive in this context may mean an identical movement is indicated a number of times consecutively, or merely that the same type of movement is indicated (e.g., moving up and then moving down) with variation in amplitude, timing, movement shape, or other properties of the repeated movement. The third criterion is that the movement should be "skillful," such that it takes a concentrated effort to perform the movement. In part to achieve these criteria, in certain embodiments of the present invention the repetitive motor movement includes multiple identical cycles of a periodic motion spanning a period of time. A display may be operated to provide an indication to prime this motor movement, and the indication can represent at least one full cycle of the repetitive motor movement. In other embodiments, the indication can represent at least 1.5 full cycles of the repetitive motor movement, or at least 2 full cycles of the repetitive motor movement. For clarity, it may be desirable to restrict the displayed indication such that less than 10 full cycles of the repetitive motor movement are indicated, or less than 6 full cycles. For example, the indication may represent between 0.5 and 8 full cycles of the repetitive motor movement, or between 1 and 6 full cycles, or between 1.5 and 4 full cycles. It will be understood that more or fewer full cycles (or portions thereof) could be indicated.

The indication may take several forms as may be deemed clinically efficacious. In some embodiments, the indicated path could be computer generated. Additionally or alternatively, the indicated path could be easily comparable to a cursor representing the current (e.g., live) performance of the patient. In various embodiments, the indicated path could be randomized, randomized within certain constraints (e.g., a sinusoid with a randomly-selected magnitude, period, offset, or other properties), or follow a non-random pattern. As such, in certain embodiments, the indication to prime a repetitive motor movement could include providing an indication (e.g., a graphical representation) of a geometric path. Non-limiting examples of such a geometric path are a linear path (e.g., positively-sloped, negatively-sloped, vertical, horizontal), a sinusoidal path, a dampened or amplified sinusoidal path, a step-function path, a circular path, and a parabolic path. The path may be continuous or discontinuous. In some embodiments, several different types of geometric paths could be used consecutively (e.g., in a serial fashion) to provide varied motor movements to increase the "skillfulness" of the task(s) and also to maintain patient interest.

In certain embodiments as otherwise described herein, the indication may include an indication of a continuous trace. In certain embodiments, the indication may include an indication of a plurality of discrete symbols, icons, or other graphical representations. The discrete symbols may be provided simultaneously with the continuous trace. Additionally or alternatively, either the discrete symbol(s) or the continuous trace, but not both, may be displayed. In some embodiments, the discrete symbols may represent selected points along the continuous trace. In certain embodiments, the discrete symbols could correspond with (e.g., be placed along) the continuous trace even though the continuous trace is not displayed (i.e., made invisible).

In various embodiments, the symbols may be part of a rewards system. In such scenarios, the method may further include (i) determining a distance between the location of the cursor and a location of a particular symbol of the plurality of discrete symbols (e.g., a nearest symbol to the cursor); (ii) determining that the distance is less than a distance threshold value; and (iii) responsive to determining that the distance is less than the distance threshold value, incrementing or decrementing a counter (e.g., a score or reward counter). This particular embodiment may be constructed to give the impression to the user (e.g., patient) that the symbols are being collected (e.g., accumulated) or redeemed. In certain embodiments, a sound could be played concurrent with (or subsequent to) the determination that the distance from the cursor to the particular symbol is less than the threshold distance. Additionally, some embodiments may include the counter as visible on the screen, in order to motivate the user and provide a sense of accomplishment. In other embodiments, the counter may be hidden in order to prevent a behavior hindering the performance (e.g., distraction). The method may further include, responsive to determining that the distance from the location of the cursor to the particular symbol is less than the threshold value, operating the display to remove at least a portion of the indication from the display. One example of this method would be the removal of the particular symbol from the display. The method may further comprise placing in the location of the removed particular symbol an alternative symbol that represents the first particular symbol as "collected" or "redeemed." One or more of the above actions may further enhance the perception by the user than the symbol are being redeemed or collected through their motor movement. In some embodiments, the indication, cursor, and operation of the display could be chosen or selected to optimize the user experience and to increase at least one of: the priming effect, the efficacy of the rehabilitation, and/or the user's desire to continue the rehabilitation.

It will be understood that there are several different ways that the signal from the sensor can be translated to (e.g., associated with) the displayed user location. In an embodiment, the user location may be determined with respect to a vertical axis or plane. This is taken to mean that the data encoded in the signal generated from the sensor that is representative of ankle angle could be used to encode the user location vertically on the display, if the display is considered a quasi-2D plane. As such, changes in the ankle angle of the user can be used to make the cursor representing the user location go "up" and "down" with respect to the display. Additionally or alternatively, the user location can be determined with respect to a horizontal axis or plane.

Additionally or alternatively, the user location could be determined based on a radial position around a central point. In such scenarios, the ankle angle could be represented/displayed on the display as a cartoon representation of the user's ankle. Additionally or alternatively, a tachometer or another type of visual representation could be utilized to measure and/or monitor a user's motor movement.

For effective placement of the cursor representing the user location, and in order to make the indication placement appropriate for individual users of varying ability (e.g., varying ankle range of motion), it may be desired to calibrate the range of the user location via a first measurement during which their maximal range and ankle angles (e.g., range of motion) is measured. In such scenarios, subsequently mapping the ankle angle signal (e.g., during a rehabilitative task or game) to the user location relative to a primed repetitive motor movement could include mapping the ankle angle signal to the user location relative to the repetitive motor movement such that 80% of the range of angles detected during the calibration period is mapped to a full range of the primed repetitive motor movement. In certain embodiments, the full range of the repetitive motor movement is determined according to the ankle signal during the calibration time period. In other embodiments, mapping the ankle angle signal, during a primed motion rehabilitation task, to the user location relative to the repetitive motor movement could be performed such that 70%, at least 60%, or some other specified fraction of the detected range of angles is mapped to a full range of the repetitive motor movement. In other embodiments, the range of possible desired user locations could correspond to between 60% and 99% of the initial maximal range or range of motion, or between 70% and 90%, or between 75% and 85%, or less than 95%, or less than 90%, or less than 85%, or greater than 60%, or greater than 75% of the full range. In some embodiments, adjustment of the user location relative to the full range may be performed to increase user comfort or increase range of motion performed during the rehabilitation period.

In order to give feedback on the user's performance of the primed motor movement, an embodiment of the invention as otherwise described herein is deriving, from the detected ankle angle signal during a primed repetitive motor movement task, a quantitative measurement of a user's performance of the repetitive motor movement. Such quantitation may be important for clinicians to evaluate the health of the user. It may also be useful for users to have a quantitative assessment of their performance. As such, it may be desired for the method to further include storing the quantitative measurement for later retrieval. This would allow user performance over time to be tracked and analyzed for progression or regression, or for changes due to other adjustments of rehabilitation treatment. It may be further desired to compare the quantitative measurement to a goal threshold and to store the result for later retrieval. The display may be further operated to indicate the result of the comparison. It may also be desired for the result of the comparison to be not displayed. In an embodiment, the quantitative measurement is representative of the accuracy with which the user performed the indicated repetitive motor movement. Accuracy may be determined as the number of times the user navigates the cursor representing the user location to within the threshold distance of a particular symbol of the plurality of discrete symbols divided by the maximum number of instances possible, expressed as a percentage. Other determinations of accuracy, as well as other metrics, may be envisioned by one of skill in the art to best represent user performance. Performances reaching the goal threshold (e.g., 90% accuracy, or 75% accuracy, or 60% accuracy, or 50% accuracy) may then be rewarded with a token or other reward. The reward may be digital or physical, and various rewards may be given for different goal thresholds. Other thresholds for successful performance may be selected as required.

In some embodiments, the systems and methods described herein may include recording and/or taking into account several periods of use to adjust operating procedures. In certain embodiments as otherwise described herein, the method may further comprise (i) operating the sensor to generate a further signal representative of ankle angle over a further period of time; (ii) during the further period of time, mapping the ankle angle signal to a user location relative to an indicated repetitive motor movement; and (iii) during the further period of time, operating the display to update the indication that represents the repetitive motor movement, wherein operating the display to update the indication that represents the repetitive motor movement includes updating a location, relative to the representation of the repetitive motor movement, of the cursor according to the user location.

An operating parameter that may be adjusted is the speed of the indication of the motor movement. For example, the speed that the user is expected to perform a repetitive motor movement may be adjusted based on the user's performance, e.g., the speed may be increased if the user performs well and decreased if the user performs poorly. As such, the method may include operating the display during a first period of time, corresponding to the performance of the repetitive motor movement task a first time, to update the indication that represents the user's performance of the repetitive motor movement such that the representation of the repetitive motor movement is translated across the display at a first speed. The method may additionally include operating the display during a second period of time, corresponding to the performance of the repetitive motor movement task a second time, to update the indication that represents the user's performance of the repetitive motor movement such that the representation of the repetitive motor movement is translated across the display at a second speed. It will be understood that other operating parameters can be adjusted between the different periods of time that correspond to different performances of a repetitive motor movement task. The method can further include determining that a quantitative measure of the user's performance during the first period of time is less than a goal threshold and, responsive to determining the quantitative measure is less than the goal threshold, operating the controller such that the second speed is less than the first speed. Similarly, the method could further include determining that the quantitative measure is greater than the goal threshold. In response to determining that the quantitative measure is greater than the goal threshold, the controller could be operated such that the second speed is greater than the first speed. In such scenarios, adjusting a respective speed according to the comparison of the quantitative measure to the goal threshold could provide a way for the user or clinician to automatically adjust the difficulty of the rehabilitation exercise in response to user performance. Among other aspects, this allows for improved rehabilitation outcomes by providing an experience that is appropriately challenging, rewarding, and engaging, instead of being overly frustrating.

Rehabilitation can be an exhausting activity, both mentally and physically. The duration of the repetitive motor movement task(s) should be selected so as to conform to the abilities of the user and also to increase gains in motor movement. This duration may be selected according to clinical data indicating increases in neuroactivity. In certain embodiments, the duration of a single repetitive motor movement task, or the cumulative duration of a set of such tasks, could be between 15 and 25 minutes, or between 18 and 22 minutes (e.g., 20 minutes). In certain embodiments, the duration could be greater than 10 minutes, or greater than 15 minutes (e.g., greater than 18 minutes, or greater than 20 minutes). In certain embodiments, the duration is less than 30 minutes, or less than 25 minutes, or less than 22 minutes. Similarly, the duration should be selected so as to conform to the abilities of the user and also to increase gains in motor movement. The duration of the repetitive motor movement task(s) may be selected according to clinical data indicating increases in neuroactivity. In certain embodiments, the duration could be between 5 and 35 minutes, or between 10 and 25 minutes (e.g., 15 minutes). In certain embodiments, the duration could be greater than 5 minutes, or greater than 10 minutes (e.g., greater than 15 minutes, or greater than 20 minutes). In certain embodiments, the duration could be less than 30 minutes, or less than 20 minutes, or less than 15 minutes. In some example embodiments, the duration of different (e.g., first and second) repetitive motor movement tasks could be equal. Alternatively, in other embodiments the duration of a first repetitive motor movement task is greater than the duration of a second repetitive motor movement task, or vice versa. It will be understood that other time periods and/or durations are possible and contemplated.

Additional gains in motor movement ability may be achieved by incorporating an interval of rest between multiple repetitive motor movement tasks. In certain embodiments, the method may also include: (i) operating the sensor to generate a further signal representative of ankle angle over a further period of time; then (ii) during the further period of time, mapping the further signal to a user location relative to the repetitive motor movement. During the further period of time, the method further includes (iii) operating the display to update the indication that represents the repetitive motor movement, wherein operating the display to update the indication that represents the repetitive motor movement includes updating a location, relative to the representation of the repetitive motor movement, of the cursor according to the user location; wherein the further period of time follows a prior period of time after an interval of rest. Similar to selecting the durations of periods during which a repetitive motor movement task is performed, the interval of rest may be selected by the clinician or user in order to increase rehabilitative results. For example, the interval of rest may be between 0.5 and 15 minutes, or between 2 and 12 minutes, or between 3 and 8 minutes, or less than 30 minutes, or less than 10 minutes (e.g., less than 5 minutes).

The rehabilitation may be enhanced by the provision of brain stimulation. The brain stimulation may be concurrent with at least one of a period of performance of a repetitive motor movement task. The brain stimulation may also be concurrent with an interval of rest, or be administered immediately before a period of performance of a repetitive motor movement task the first period of time or immediately after such a period. Examples of possible brain stimulation techniques could include sound (e.g., particular notes or music, a particular rhythm or volume), direct vibration (e.g., a vibrating wearable such as a bracelet), electrical stimulation (e.g., to the leg), and magnetic stimulation (e.g., to the brain). It may be desirable for one mode of stimulation to be used in a clinical setting while another mode is used when the treatment is done outside of a clinical setting (e.g., at home). It will be understood that other suitable techniques are possible and contemplated.

Beneficially, rehabilitation exercises may be designed to be minimally invasive while building the targeted abilities. Accordingly, in certain embodiments, the ankle may be permitted to rotate around more than one axis. This allows for a lighter, more portable ankle angle sensor (e.g., a sensor that consists of a small sensor module and a strap used to attach the sensor module to a user's foot) and also provides the user with a way to develop ancillary, stabilizing control of the ankle beyond the single measured degree of motion. Depending on user ability, in some scenarios, the ankle may be free to rotate around exactly two axes, or to freely rotate around any axis.

Regardless of the degrees of freedom associated with ankle rotation, in some examples, systems and methods described herein may only measure and display the rotation around or about a single axis. To this end, the sensor could be configured to detect ankle rotation about a given axis. Alternatively, the sensor can be configured to generate t signals from the ankle rotation based about a single axis. This approach may provide the measurement of only the desirable motion and discards information about other ankle rotations that the user may be instructed to avoid.

Often, a hindrance to effective rehabilitation is discomfort associated with performing the exercise which leads to an aversion to continued rehabilitation. To help remedy this, in certain embodiments the sensor could be integrated into a garment (e.g., a sock, a compression sock, a shoe, a boot, a sandal, an ankle band, an ankle brace, etc.). Integration with a familiar object could improve ease of use and increase comfort level for the user. The garment may also be designed to mimic realistic ankle support, such as that typically provided by a shoe or sock in everyday conventional use.

FIG. 7 and FIG. 8 display two views of an example embodiment wherein the system additionally includes a heel rest, and wherein the sensor (e.g., an accelerometer, a bend sensor) is incorporated into a garment. The heel rest allows ankle elevation, allowing for a full range of motion. In the displayed example embodiment, the user wears a garment (e.g., an ankle brace) with at least one sensor incorporated. Examples of the sensor locations are shown by the dashed lines. For example, a flex sensor may be incorporated (e.g., sewn or otherwise adhered to/within the material of the ankle brace or other garment). Some possible modes of ankle motion are shown by double-ended arrows. The sensor may be configured to measure one or more of these modes.

It will be understood that the display may be operably connected to a variety of devices. In some embodiments, the ankle angle signals, and/or other information, such as calibration data or other user-specific data could be transmitted and received by way of a wireless communication link. In certain embodiments, the display could be operably connected to at least one of a smartphone, tablet, laptop computer, or another computing device adapted to receive wireless input signals. It may be desired for the sensor to be operably connected to a device that is portable and/or inexpensive. In certain embodiments, the sensor could be operably connected to a smartphone or smart watch.

It will be understood that a variety of techniques could be utilized to measure ankle angle. Examples of possible sensors could include sensors comprising a flex sensor, comprising a gyroscope, comprising an accelerometer, and comprising a depth sensor. In certain embodiments the sensor includes more than one sensor type. In some embodiments, inclusion of more than one sensor type may beneficially increase data resolution and/or data reliability. More than one sensor type may also provide valuable information beyond what is included in the first, second, and third signals.

II. Example Systems

Figure 2:
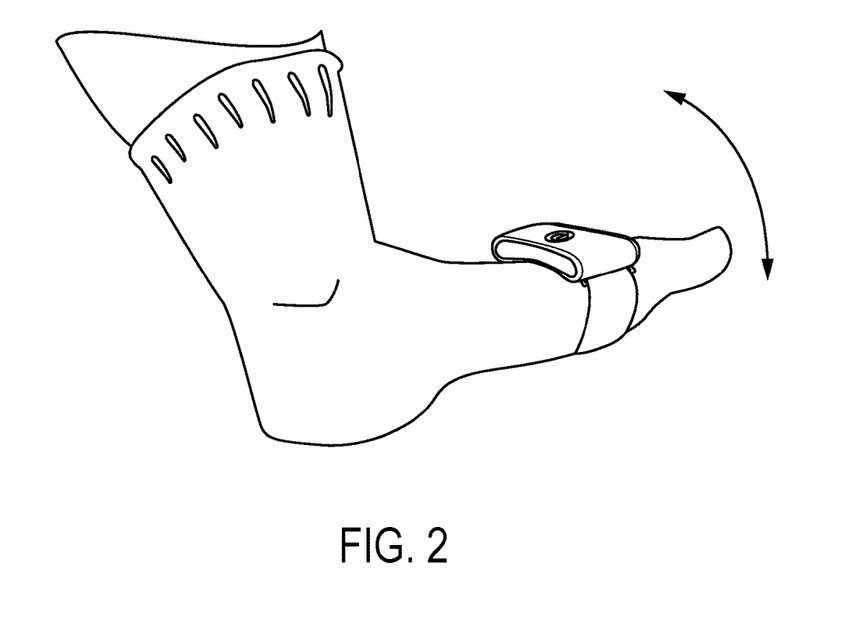
FIG. 2 illustrates a movement tracking device, according to an example embodiment.
Figures 3A, 3B:
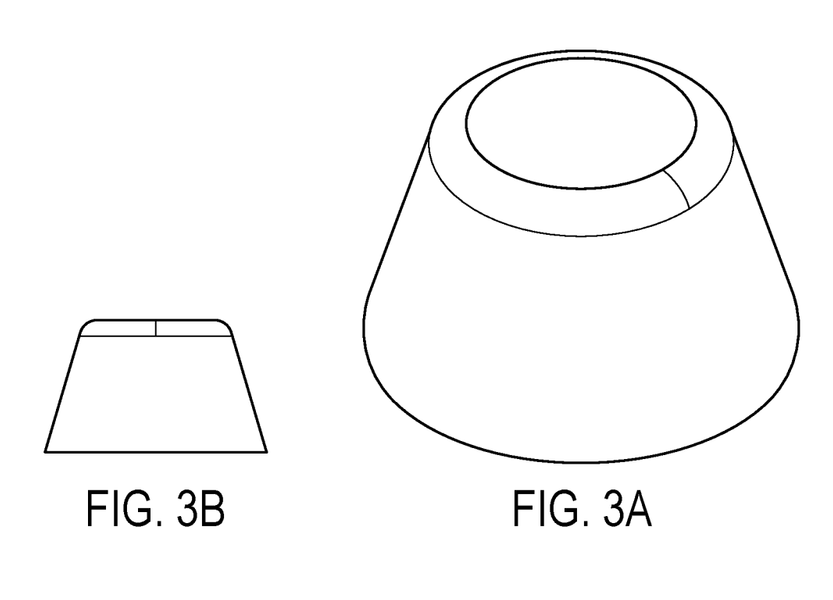
FIG. 3A through 3E illustrate various view of a heel resting device, according to an example embodiment.
Figures 3C, 3D:
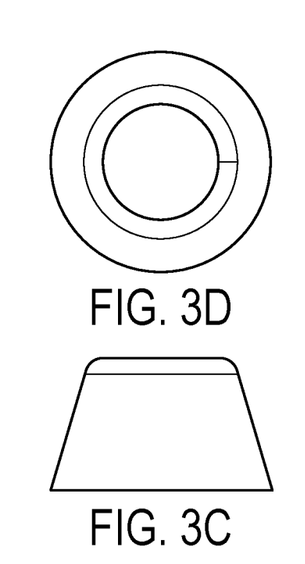
Figure 3E:
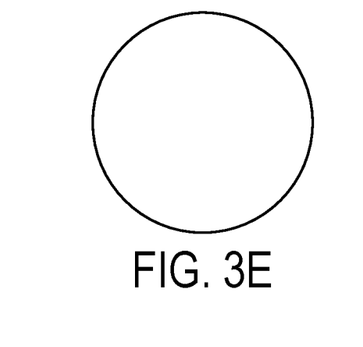
Figures 4A, 4B, 4C, 4E:
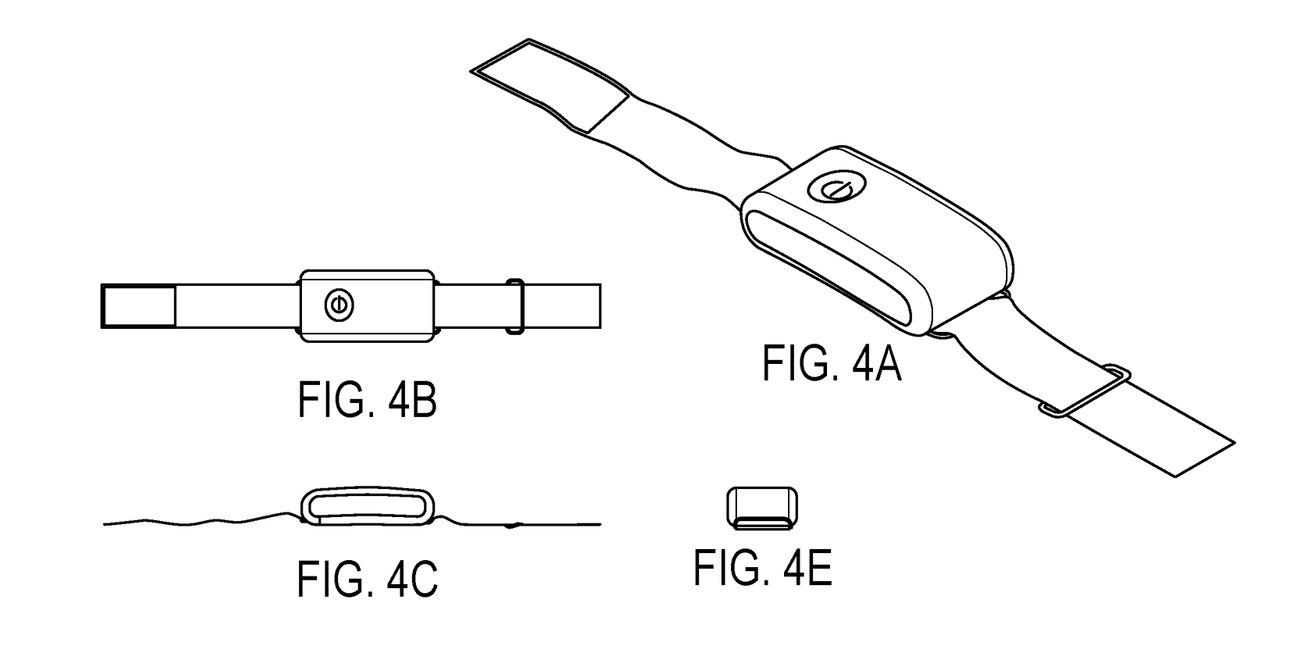
FIG. 4 illustrates a movement tracking or sensing device, according to an example embodiment.
Figure 4D:
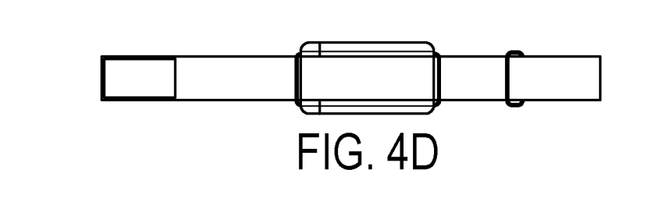

FIG. 2 illustrates an exemplary embodiment of a sensing device configured for selective use by a patient. To this end, the sensing device can be configured of any suitable design or material, and can include an adjustable or expandable strap for connecting the device to a movable patient part, such as the foot. Alternatively, one or more sensing devices, or sensing mechanism(s), can be integrally formed in an expandable fabric device selectively worn by the patient, such as a tube or sock, or any other suitable configuration.

The systems and methods described herein could provide a way to "gamify" a rehabilitation activity. Such a game can be configured and adapted to provide priming information visually to the patient during operation of the system by coordinating a correct movement based on the pre-game range of motion determined for the patient, and then display a trace of the real time patient input data to help the patient aim toward and see the correct movement information. Various versions or embodiments of the instructional game can start by measuring the user's range of foot dorsiflexion and plantarflexion using a sensing device attached to the patient to input the data. These measurements can be incorporated by the instructional gameplay to adjust the output and extent of the priming exercise based on the ability of the patient to allow patients with varied ranges of motion to operate the system and play the priming exercises successfully.

In an embodiment, the priming information delivered visually to the patient includes movements directed to ankle dorsiflexion and plantarflexion to control a trace that shows the movement of the patient compared to a target movement stored in the processor. A number of desired repeated motions can function as the target movement for the patient that results in a priming outcome when coupled with the visual information received while playing a game.

Figure 1A:
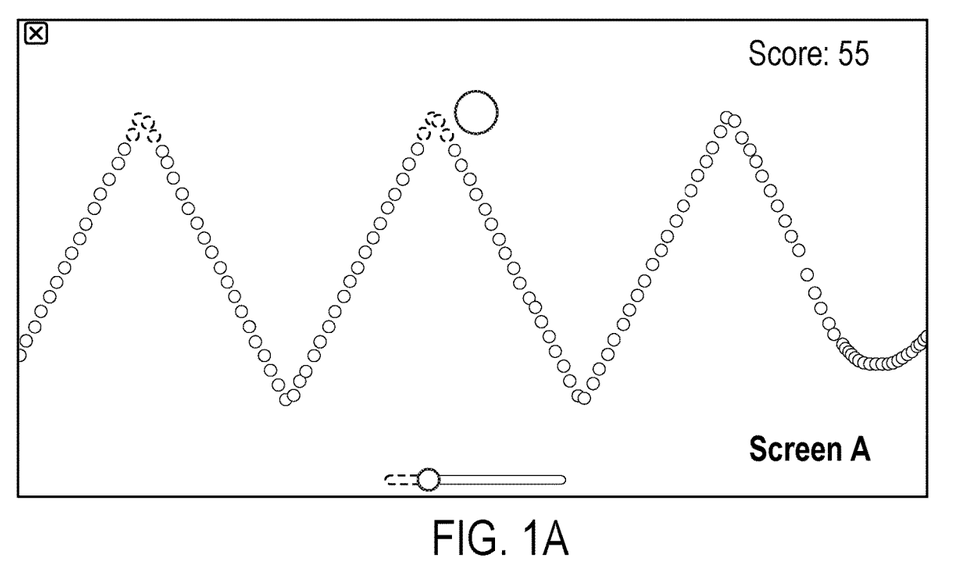
FIGS. 1A through 1I illustrate various screens that may be displayed, according to example embodiments.

As illustrated in FIG. 1A (e.g., Screen A), the target movement can be an object moving through a 2D side-scrolling obstacle course. The course can be composed of small dots that appear in waveforms, including a sine wave, squares, saw tooth wave, and triangles, for example. When the patient's circle hits a dot, the device can vibrates to provide haptic feedback, or provide visual information indicating to the patient that they have performed the and the dot changes color from red to green. At the end of the game, the patient is shown the percent of dots collected.

In accordance with the present disclosure, another priming version of the instructional game can be similar to the basic game with additions including narrative elements, cartoon-style visuals, avatar customization, and the ability to collect and display items to further engage the patient and help the patient to focus during activity. In this version of the instructional game, the patient can select activities and receive messages presenting a choice of priming exercises.

Figure 1B:
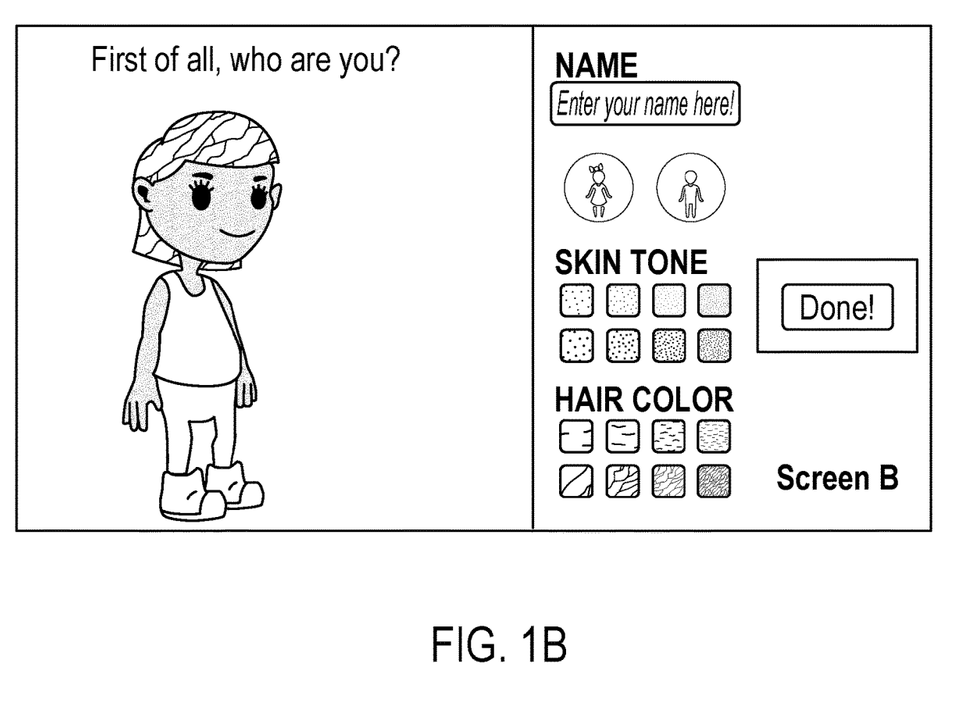

As illustrated in FIG. 1B (e.g., Screen B), the patient may customize an "avatar," a cartoon representation of the patient, by providing their name and gender and choosing one of eight skin tone options and one of eight hair color options. It will be understood that other types of customizations and/or personalization may be possible and contemplated.

Figure 1C:
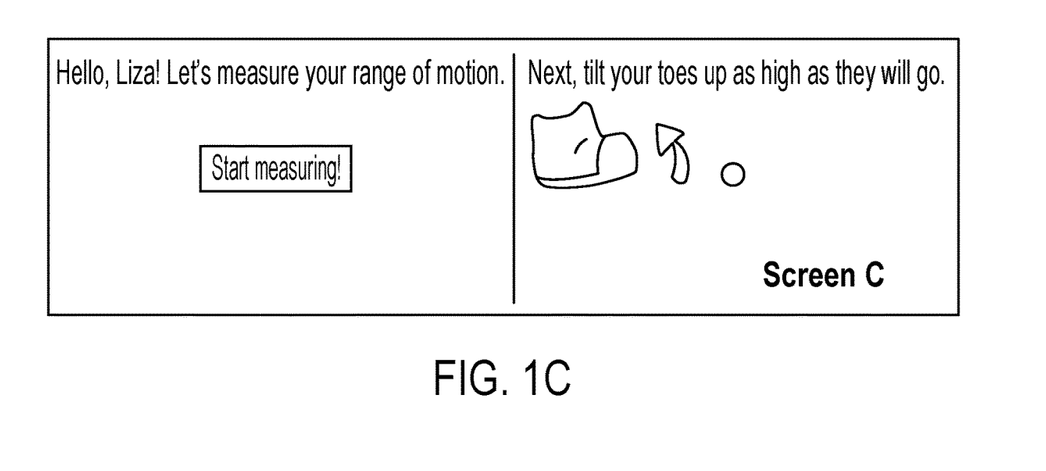

After the system is configured for use by the patient in any embodiment, the range of motion of the patient can be measured by the system, as shown in FIG. 1C (e.g., Screen C). In this embodiment, the patient can be guided by a brightly colored shoe, for example.

Figure 1D:
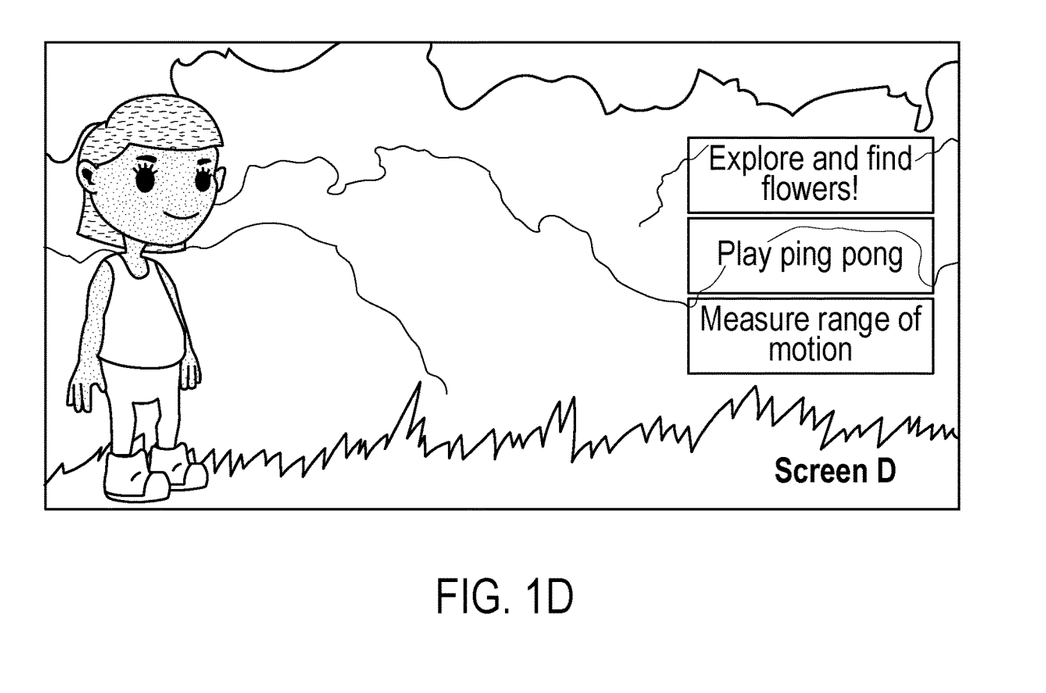
Figure 1E:
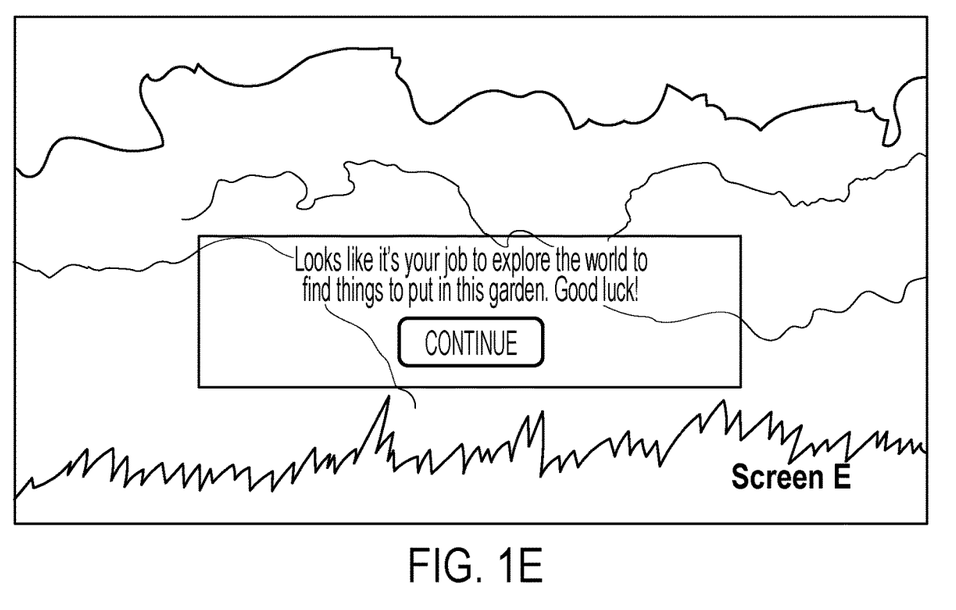

After their range of motion has been measured and saved, the patient can select a priming exercise game in some embodiments, or a preselected priming exercise game can start automatically or based on an input from the patient. In an embodiment, the game can present options to the patient such as "Explore and find flowers," "Play ping pong," or re-measure your range of motion, as shown in FIG. 1D, (e.g., Screen D) below. The output display can include transitions that change information to help maintain attention to the visual display, as seen from the change in background color of Screen D to FIG. 1E, (e.g., Screen E), for example.

Figure 1F:
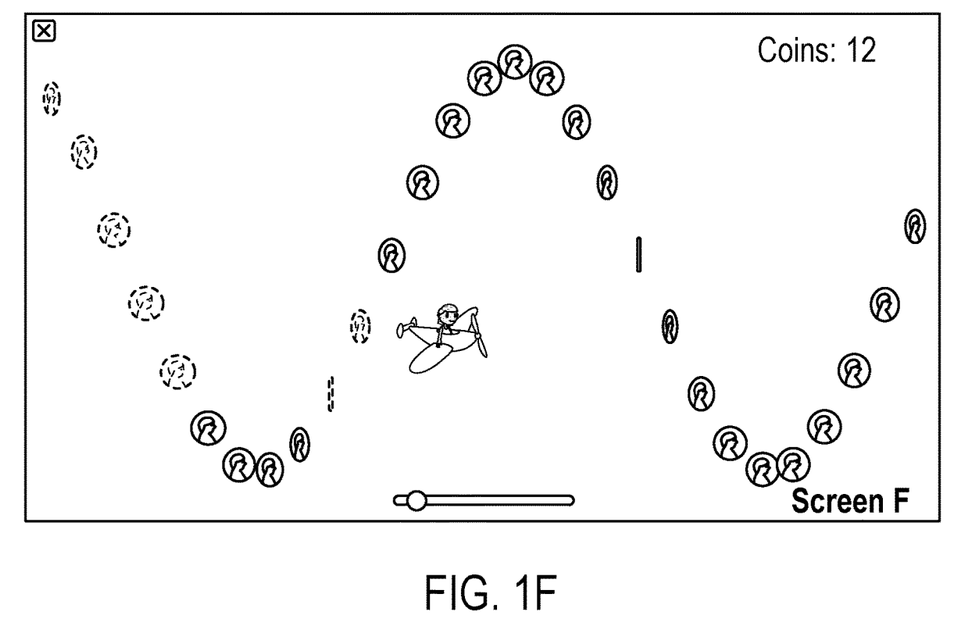

In an embodiment shown in FIG. 1F (e.g., Screen F), a 2D side-scrolling obstacle course can be presented with visual output information demonstrating correct movement for the priming exercise. In this embodiment, the display can indicate which visual targets the patient has negotiated successfully such as by transforming the coins to white dotted circles, for example. In this embodiment, the patient can use their priming exercise movements to control a cartoon plane with their avatar in it, and they collect coins that are arranged in patterns when they perform the priming exercise successfully.

Figure 1G:
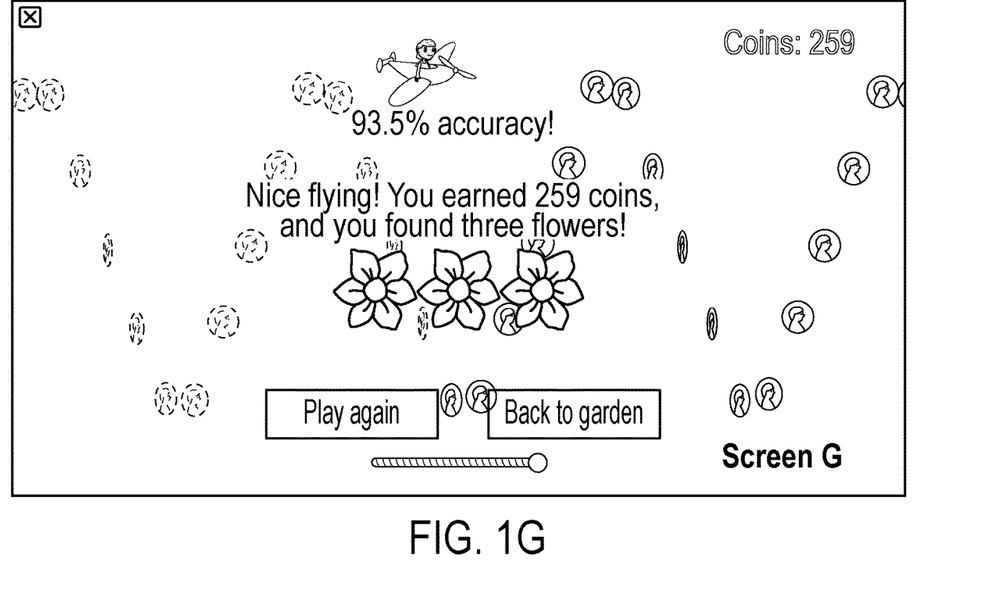

At the end of the game, the system can display the percent of coins collected during the session, if desired, and can also reward the patient with flowers based on their performance, or display other feedback to the patient as desired. For example, if the patient scores above 95% in the side-scrolling priming exercise, they can earn five flowers; if they score above 75%, they can earn three flowers; if they score above 50%, they can earn two flowers; and any other score can be rewarded with one flower, for example, as shown in FIG. 1G (e.g., Screen G).

Figure 1H:
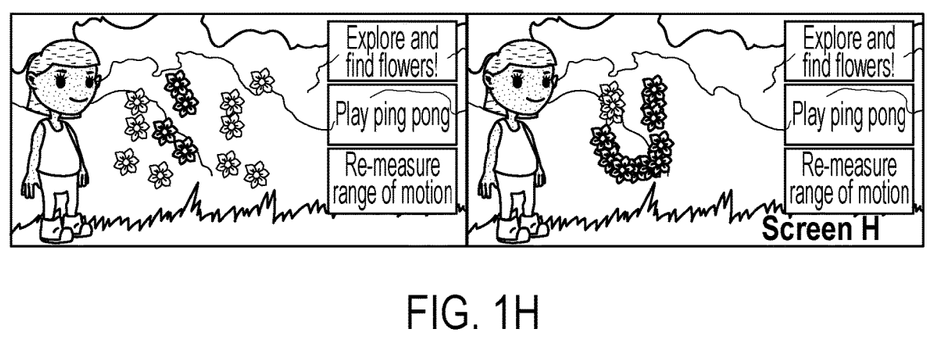

After a selected priming exercise is complete, the patient can perform various relaxing exercises or engage in fun activities with the system to further encourage engagement, for example, as shown in FIG. 1H (e.g., Screen H).

Figure 1I:
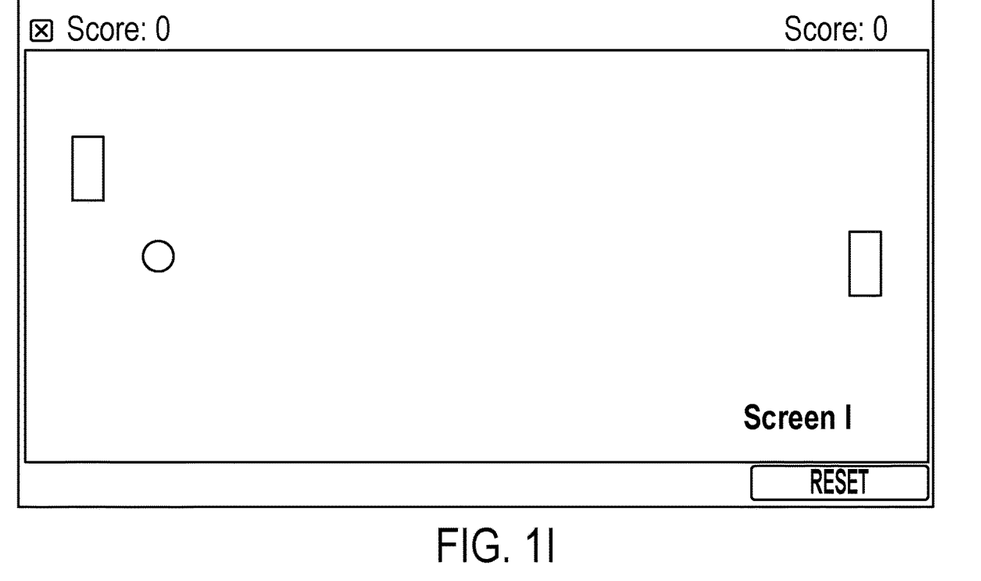

Other priming games can guide the patient through other priming exercises, as shown in FIG. 1I (e.g., Screen I), for example. Here the patient can play a game of ping pong against a computer opponent. In this game, the patient can use their ankle movements to move a small, graphical representation of a ping pong paddle up and down. Although this game does not require as much consistent ankle movement as the side-scroller game, it is engaging and can provide patients with a fun change of pace from the side-scroller game while still providing a priming visual output regarding correct movement for flexing the foot.

Embodiments of a system constructed in accordance with the principles herein for a priming ankle rehabilitation system for stroke patients can increase user motivation, exercise compliance, and improve movement outcomes based on the combined physical and cognitive stimulation provided by the system.

The underlying problem solved with a system constructed in accordance with the principles of the present invention is the low motivation and the difficulty of attending in-person physical therapy sessions for the post-stroke patient. The impaired condition of patients post-stroke often prevents them from completing needed physical therapy as recommended. For this reason, engaging systems that achieve better rehabilitation results and provide portable options for the patients are needed to improve the short and long term outcome of this patient population.

In an embodiment, an exemplary interface for the system can enable multiple people to work on the game in different roles for the sake of efficiency, or can enable social media and group play by the patients. Other embodiments use engaging, visually appealing priming games to present priming information and exercises to patients that are also clinically useful.

In order to maximize comfort and provide an exact starting point and baseline for the patient, an exemplary system constructed in accordance with the principles herein can include a heel rest as illustrated in FIGS. 3A through 3E below.

In certain embodiments, the priming game can be played on a tablet or other suitable mobile device. Other embodiments using projected imagery or glasses adapted to receive input from a processor are contemplated as well.

A suitable sensing device constructed in accordance with the principles of the present disclosure can include a number of possible designs. One exemplary design, shown in FIGS. 4A though 4E allows for an expandable or adjustable material to selectively connect a sensor or other suitable movement tracking output device to the foot of a patient in order to operate a system constructed in accordance with the principles herein.

Figure 5:
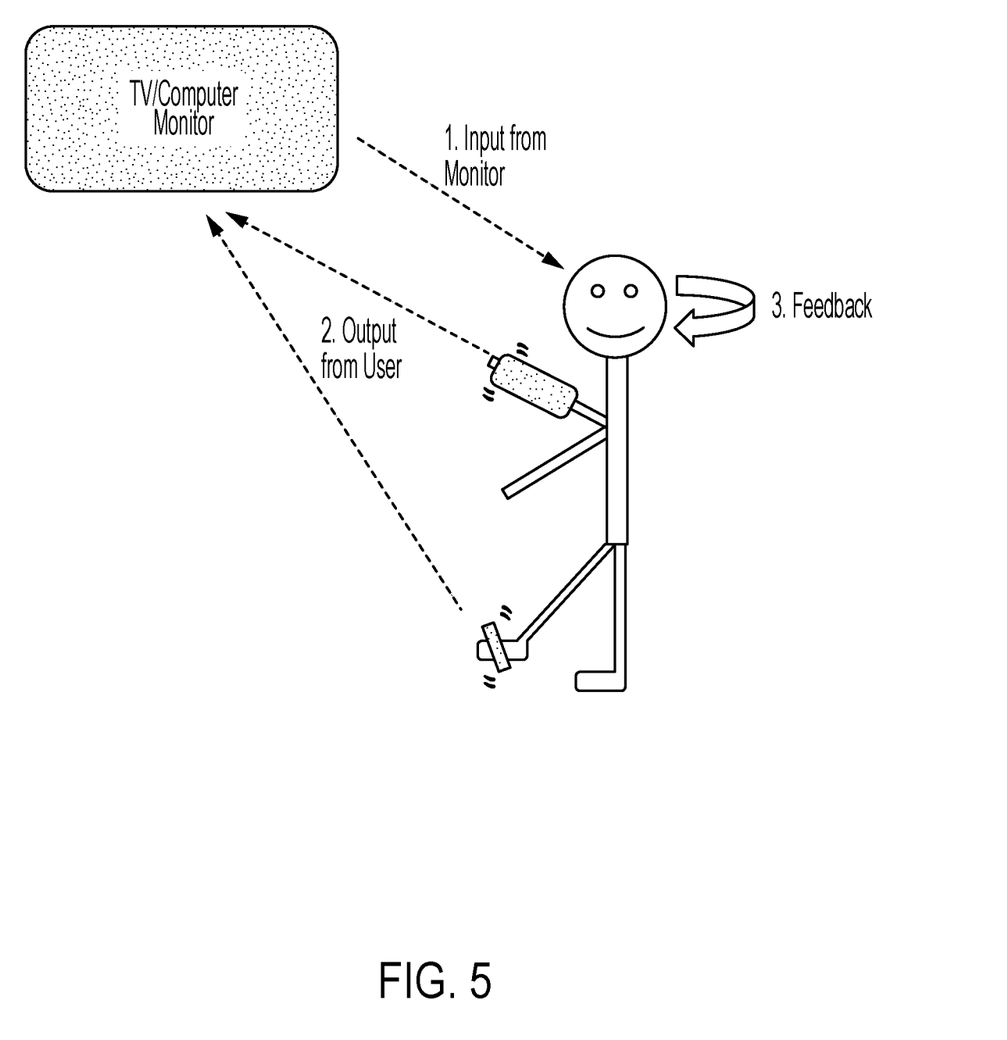
FIG. 5 illustrates a system including a wireless patient controller, according to an example embodiment.
Figure 6:
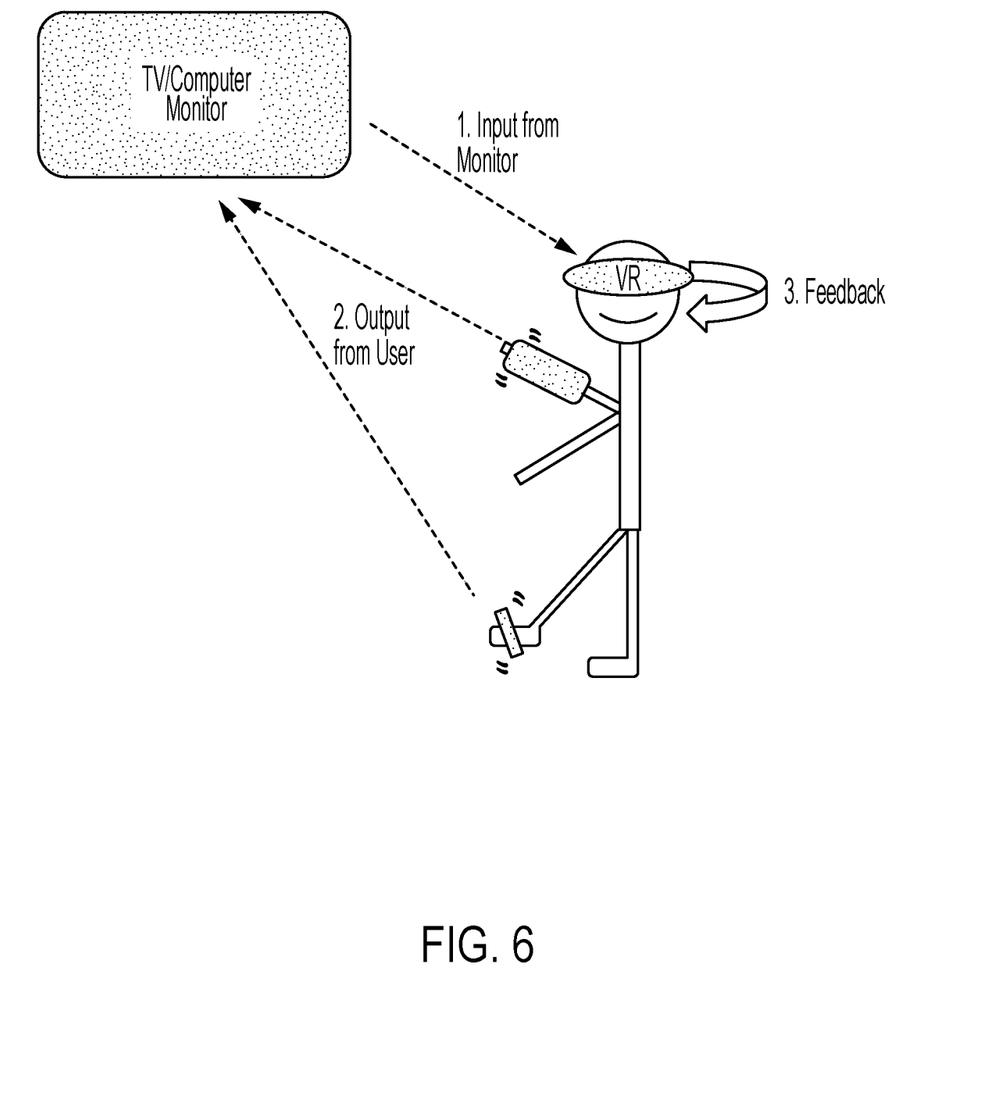
FIG. 6 illustrates a system including a connectable VR system, according to an example embodiment.

As illustrated in FIGS. 5 and 6, exemplary systems constructed in accordance with the principles herein can include bidirectional devices for communicating feedback, messages, or instructions during use of the system. Further, outputs from the system can be used to analyze and modify other connectable devices, such as VR systems or other devices that can be employed to further teach the priming information beyond or after the system herein provides the priming exercises to the patient. To this end, a progress bar can be displayed, if desired, during operation of the system such that patient progress through a priming game can be coordinated for stops and starts with the patient input, allowing for possible interruptions during operation of the system. In certain embodiments, the system can include a suitable sensor reader. Further, scene transition buttons and other modifications input by clinicians and or patients can provide direction to the exercises to work toward achieving a proposed clinical outcome. For example, clinicians could modify the length, settings and difficulty of priming games of the system. Additionally, clinicians can decide if less than fully unrestricted motion but greater flexibility than fully restricted motion is recommended for a given patient, and modifications of the system herein could include devices to match the desired clinical performance, such as partially restricted sensor systems.

Systems constructed in accordance with the principles herein can further provide error feedback to the patient, if desired. For example, if the device is unplugged or the connection is otherwise not working for at least three seconds at the start of the scene, an error message can appear on the screen with instructions on how to repair the connection and a button to restart the scene.

III. Conclusion

The above detailed description describes various features and functions of the disclosed systems, devices, and methods with reference to the accompanying figures. In the figures, similar symbols typically identify similar components, unless context indicates otherwise. The illustrative embodiments described in the detailed description, figures, and claims are not meant to be limiting. Other embodiments can be utilized, and other changes can be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

The computer-readable medium may also include non-transitory computer-readable media such as computer-readable media that stores data for short periods of time like register memory, processor cache, and/or random access memory (RAM). The computer-readable media may also include non-transitory computer-readable media that stores program code and/or data for longer periods of time, such as secondary or persistent long term storage, like read only memory (ROM), optical or magnetic disks, and/or compact-disc read only memory (CD-ROM), for example. The computer-readable media may also be any other volatile or non-volatile storage systems. A computer-readable medium may be considered a computer-readable storage medium, for example, or a tangible storage device.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

IV. Enumerated Example Embodiments

Embodiments of the present disclosure may thus relate to one of the enumerated example embodiments (EEEs) listed below. It will be appreciates that features indicated with respect to one EEE can be combined with other EEEs.

EEE 1 is a system for priming an injured patient for physical therapy using visually driven priming motor movement comprising: (i) a display configured to transmit a series of priming instructional data stored in a memory of the system and selectively output to the display during operation of the system, the series of priming instructional data forming an output display of correct patient motor movement for a priming exercise; (ii) a processor operatively connected to the memory of the system; (iii) the processor configured to compute a calibration input from a baseline position; (iv) the calibration input including an analysis of patient data input concerning a range of motion for the patient from the baseline position and calibration data stored in the memory of the system; (v) the processor configured to adjust the speed, length and difficulty of the output display based on at least one of the calibration input, motor movement input data received from a motor movement sensing device of the system during operation, or other input; (vi) the motor movement sensing device configured to track and transmit motor movement by the patient in three dimensions during operation of the system; (vii) the system configured to output to the display and generate a trace on the display of x and y components of the motor movement data received in real-time from the motor movement sensing device of the system relative to the output display of correct patient motor movement for the priming exercise to form a visual mapping display including both the real-time x and y components of the data from the patient compared to the correct patient motor movement for the priming exercise; (viii) the display screen selectively displaying additional patient inputs to the system via a voice, keyboard, or other input device during set up and/or operation of the system; and the system configured to deliver at least one stimulation input to the patient during operation of the system.

EEE 2 is the system of EEE 1, wherein the output display configured to selectively generate and display audio and visual information related to patient awards earned based on motor movement input data received during operation of the system that correlates to the correct patient motor movement for the priming exercise for a pre-selected time period.

EEE 3 is the system of EEE 1, wherein the at least one stimulation input comprising at least one of an audio track, white noise, vibration source (e.g., Thera bracelet), functional electric stimulator (FES), music, and brain stimulator.

EEE 4 is the system of EEE 2, wherein display of information related to patient awards earned based on motor movement input data received during operation of the system includes converting a visual element of the output display to temporarily display a rotating gold coin.

EEE 5 is the system of EEE 1, wherein the display, processor and memory are operably connected in at least one of a smart phone, tablet, computer, or other processing and storage device having an interface, and including a component adapted to receive wireless input signals.

EEE 6 is the system of EEE 1, wherein one or more of a motor or cognitive deficit is visually mapped via the output display for the priming exercise.

EEE 7 is the system of EEE 1, wherein the exercise plane for performing the priming exercise is unrestricted and measured from the baseline to reduce fatigue.

EEE 8 is the system of EEE 1, wherein the output display is portable.

EEE 9 is the system of EEE 1, wherein the motor movement sensing device further comprises a sensor secured to a strap, the strap configured for selectively securing the sensor on a moveable body part of the patient.

EEE 10 is the system of EEE 1, wherein the motor movement sensing device further comprises a motion sensor integrated into a sock, slipper, or other wearable device.

EEE 11 is the system of EEE 1, further comprising a button or command to restart the system from the point of operation when the system received the last input data from the patient.

EEE 12 is the system of EEE 1, wherein the visual mapping display includes additional memory mapping data from the system.

EEE 13 is the system of EEE 1, further comprising an elevation device configured to provide a comfortable base for the patient to rest the baseline engaging body part during operation of the system.

EEE 14 is a visual mapping output for a cognitive or motor injury based on data analyzed and presented on a display system from a remote sensor selectively secured to a moveable patient body part.

EEE 15 is the system of EEE 1, wherein the motor movement sensing device further comprises a sensor secured to a strap, the strap configured for selectively securing the sensor on a movable body part of the patient.

EEE 16 is the system of EEE 1, wherein the motor movement sensing device further comprises a flex sensor.

EEE 17 is the system of EEE 1, wherein the visual mapping display includes additional memory mapping data from the system.

EEE 18 is the system of EEE 1, further comprising an elevation device configured to provide a comfortable base for the patient to rest the baseline engaging body part during operation of the system.

EEE 19 is a visual mapping output for a cognitive or motor injury based on data analyzed and presented on a display system from a remote sensor selectively secured to a moveable patient body part.

EEE 20 is a tele-rehabilitation system comprising: (i) tracking outputs generated by and transmitted to patient priming exercise tracking device(s) systems configured to allow the patient and/or clinician to track progress and send or display signals to patients to keep up with their exercises; and (ii) a dashboard operably connected to the tracking outputs warning the patient that the patient is not complying with the prescribed exercises.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

I claim:

1. A method for improved rehabilitation of ankle motion for the treatment of stroke by visually-driven priming of motor movement, the method comprising:
    operating a sensor that is coupled to a foot or ankle by way of a strap or an expandable fabric garment to generate a first signal representative of ankle angle over a first period of time;
    determining, based on the first signal, a range of angles detected over the first period of time;
    prior to a second period of time, operating a display to provide an indication to prime a repetitive motor movement, wherein the indication represents at least one full cycle of the repetitive motor movement with respect to ankle angle as a function of time;
    operating the sensor to generate a second signal representative of ankle angle over the second period of time;
    during the second period of time, mapping the second signal to a user location with respect to ankle angle relative to the repetitive motor movement; and
    during the second period of time, operating the display to update the indication that represents the repetitive motor movement, wherein operating the display to update the indication that represents the repetitive motor movement includes updating a location, relative to the representation of the repetitive motor movement, of a cursor according to the user location.

2. The method of claim 1, wherein the repetitive motor movement consists of multiple identical cycles of a periodic motion spanning the second period of time.

3. The method of claim 2, wherein providing an indication to prime a repetitive motor movement comprises at least one of: (i) providing an indication that represents at least 1.5 full cycles of the repetitive motor movement, (ii) providing an indication of a geometric path, (iii) providing an indication of a continuous trace, or (iv) providing an indication of a plurality of discrete symbols.

4. The method of claim 1, wherein providing an indication to prime a repetitive motor movement comprises providing an indication of a plurality of discrete symbols, and wherein the method further comprises:
    determining a distance between the location of the cursor and a location of a particular symbol of the plurality of discrete symbols;
    determining that the distance is less than a distance threshold value; and
    responsive to determining that the distance is less than the distance threshold value, incrementing or decrementing a counter.

5. The method of claim 4, further comprising:
responsive to determining that the distance is less than the distance threshold value, operating the display to remove at least a portion of the indication from the display.

6. The method of claim 1, wherein mapping the second signal to the user location relative to the repetitive motor movement comprises mapping the second signal to the user location relative to the repetitive motor movement such that 80% of the detected range of angles is mapped to a full range of the repetitive motor movement.

7. The method of claim 1, further comprising deriving, from the second signal, a quantitative measurement of a user's performance of the repetitive motor movement.

8. The method of claim 1, wherein the method further comprises:
operating the sensor to generate a third signal representative of ankle angle over a third period of time;
during the third period of time, mapping the third signal to a user location relative to the repetitive motor movement; and
during the third period of time, operating the display to update the indication that represents the repetitive motor movement, wherein operating the display to update the indication that represents the repetitive motor movement includes updating a location, relative to the representation of the repetitive motor movement, of the cursor according to the user location.

9. The method of claim 8, wherein operating the display during the second period of time to update the indication that represents the repetitive motor movement comprises updating the indication such that the representation of the repetitive motor movement is translated across the display at a first speed and wherein operating the display during the third period of time to update the indication that represents the repetitive motor movement comprises updating the indication such that the representation of the repetitive motor movement is translated across the display at a second speed that differs from the first speed.

10. The method of claim 9, further comprising determining that a quantitative measure of a user's performance of the repetitive motor movement is less than a goal threshold and, responsive to determining that the quantitative measure is less than the goal threshold, operating the display such that the second speed is less than the first speed.

11. The method of claim 9, further comprising determining that a quantitative measure of a user's performance of the repetitive motor movement is greater than a goal threshold and, responsive to determining that the quantitative measure is greater than the goal threshold, operating the display such that the second speed is greater than the first speed.

12. The method of claim 1, wherein the method further comprises:
operating the sensor to generate a third signal representative of ankle angle over a third period of time;
during the third period of time, mapping the third signal to a user location relative to the repetitive motor movement; and
during the third period of time, operating the display to update the indication that represents the repetitive motor movement, wherein operating the display to update the indication that represents the repetitive motor movement includes updating a location, relative to the representation of the repetitive motor movement, of the cursor according to the user location;
wherein the third period of time follows the second period of time after an interval of rest.

13. The method of claim 12, wherein at least one of: (i) the second period of time is between 18 and 22 minutes, (ii) the third period of time is between 8 and 12 minutes, or (iii) the interval of rest is between one and three minutes.

14. The method of claim 1, wherein the method further comprises providing brain stimulation concurrent with at least one of the first period of time, second period of time, and third period of time, wherein the brain stimulation is sound, direct vibration, electrical stimulation, or magnetic stimulation.

15. The method of claim 1, wherein the ankle is permitted to rotate around more than one axis and wherein the sensor detects ankle rotation only around a single axis.

16. The method of claim 1, wherein the sensor is integrated into a garment.

17. The method of any of claim 1, wherein the sensor comprises at least one of: (i) a flex sensor, (ii) a gyroscope, (iii) an accelerometer, or (iv) a depth sensor.

18. A non-transitory computer-readable medium, having stored thereon program instructions that, upon execution by a controller, cause the controller to perform operations of a method for rehabilitation of ankle motion for the treatment of stroke comprising:
operating a sensor that is coupled to a foot or an ankle by way of a strap or an expandable fabric garment to generate a first signal representative of ankle angle over a first period of time;
determining, based on the first signal, a range of angles detected over the first period of time;
prior to a second period of time, operating a display to provide an indication to prime a repetitive motor movement, wherein the indication represents at least one full cycle of the repetitive motor movement with respect to ankle angle as a function of time;
operating the sensor to generate a second signal representative of ankle angle over the second period of time;
during the second period of time, mapping the second signal to a user location with respect to ankle angle relative to the repetitive motor movement; and
during the second period of time, operating the display to update the indication that represents the repetitive motor movement, wherein operating the display to update the indication that represents the repetitive motor movement includes updating a location, relative to the representation of the repetitive motor movement, of a cursor according to the user location.

19. The non-transitory computer-readable medium of claim 18, wherein operating the display during the second period of time to update the indication that represents the repetitive motor movement comprises updating the indication such that the representation of the repetitive motor movement is translated across the display at a first speed, and wherein the operations further comprise:
operating the sensor to generate a third signal representative of ankle angle over a third period of time;
during the third period of time, mapping the third signal to a user location relative to the repetitive motor movement; and
during the third period of time, operating the display to update the indication that represents the repetitive motor movement, wherein operating the display to update the indication that represents the repetitive motor movement includes updating a location, relative to the representation of the repetitive motor movement, of the cursor according to the user location, and wherein operating the display during the third period of time to update the indication that represents the repetitive motor movement comprises updating the indication such that the representation of the repetitive motor movement is translated across the display at a second speed that differs from the first speed.

20. The non-transitory computer-readable medium of claim 19, further comprising at least one of: (i) determining that a quantitative measure of a user's performance of the repetitive motor movement is less than a goal threshold and, responsive to determining the quantitative measure is less than the goal threshold, operating the display such that the second speed is less than the first speed, or (ii) determining that a quantitative measure of a user's performance of the repetitive motor movement is greater than a goal threshold and, responsive to determining the quantitative measure is greater than the goal threshold, operating the display such that the second speed is greater than the first speed.

* * * * *